United States Patent
Tedone

(10) Patent No.: US 11,464,753 B2
(45) Date of Patent: Oct. 11, 2022

(54) COMPOSITION FOR TREATMENT OF NEURODEGENERATIVE DISEASE

(71) Applicant: WINNING THE FIGHT INC., Lutz, FL (US)

(72) Inventor: Vincent M Tedone, Tampa, FL (US)

(73) Assignee: Tedone 3G LLC, Tampa, FL (US)

( * ) Notice: Subject to any disclaimer, the term of this patent is extended or adjusted under 35 U.S.C. 154(b) by 250 days.

(21) Appl. No.: 16/252,212

(22) Filed: Jan. 18, 2019

(65) Prior Publication Data
US 2019/0151275 A1 May 23, 2019

Related U.S. Application Data

(63) Continuation of application No. 14/652,345, filed as application No. PCT/US2014/013002 on Jan. 24, 2014, now abandoned.
(Continued)

(51) Int. Cl.
*A61K 31/122* (2006.01)
*A61K 31/19* (2006.01)
(Continued)

(52) U.S. Cl.
CPC .......... *A61K 31/205* (2013.01); *A61K 31/122* (2013.01); *A61K 31/19* (2013.01); *A61K 31/194* (2013.01); *A61K 31/197* (2013.01); *A61K 31/22* (2013.01); *A61K 31/7084* (2013.01); *A61K 45/06* (2013.01); *A61K 2300/00* (2013.01)

(58) Field of Classification Search
CPC ................ A61K 31/205; A61K 31/122; A61K 31/7084; A61K 31/194; A61K 31/197; A61K 45/06; A61K 31/22; A61K 31/19; A61K 2300/00
See application file for complete search history.

(56) References Cited

U.S. PATENT DOCUMENTS

| | | | | |
|---|---|---|---|---|
| 2006/0292134 | A1* | 12/2006 | Stohs | A61K 31/715 424/94.1 |
| 2010/0279943 | A1* | 11/2010 | Zisapel | A61K 31/194 514/17.8 |
| 2011/0020443 | A1* | 1/2011 | Liu | A61P 25/28 424/464 |

FOREIGN PATENT DOCUMENTS

| | | | | |
|---|---|---|---|---|
| WO | WO-2006016828 A2 | * | 2/2006 | ............. A61P 25/28 |
| WO | WO-2012112340 A2 | * | 8/2012 | ............. A23K 20/30 |
| WO | WO-2012136587 | * | 10/2012 | |

OTHER PUBLICATIONS

Glutamate Transporters in Neurologic Disease Maragakis et al. American Medical Association (Year: 2001).*

* cited by examiner

*Primary Examiner* — Blaine Lankford
*Assistant Examiner* — Lauren K Van Buren
(74) *Attorney, Agent, or Firm* — Christopher Paradies; Paradies Law P.A.

(57) ABSTRACT

A composition of matter comprising an α-ketoglutarate (AKG) or an α-ketoglutaric acid or a salt of an α-ketoglutarate may be used to treat patients having a neurodegenerative disease, such as amyotrophic lateralsclerosis. The composition may be administered hourly or may be administered once a day depending on the size and activity of the patient and the release coating or mechanism provided. In addition to AKG, a core composition may comprise GABA and a source of coenzyme Q10. Other substances may be provided either orally or intravenous in addition to the core composition, as required to control symptoms, or in order to stimulate stem cells to add motor neurons.

13 Claims, 3 Drawing Sheets

Related U.S. Application Data

(60) Provisional application No. 61/756,824, filed on Jan. 25, 2013.

(51) Int. Cl.
*A61K 31/194* (2006.01)
*A61K 31/197* (2006.01)
*A61K 31/205* (2006.01)
*A61K 31/22* (2006.01)
*A61K 31/7084* (2006.01)
*A61K 31/06* (2006.01)
*A61K 45/06* (2006.01)

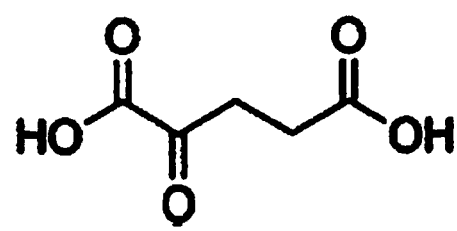
FIG. 1
FIG. 2 (Idebenone)
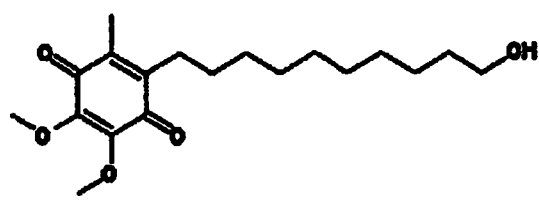
FIG. 3 (Ubiquinol)
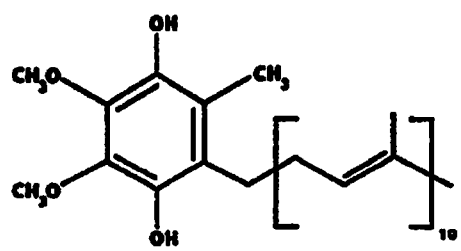

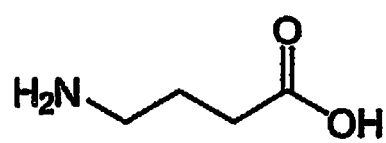
FIG. 5
FIG. 6
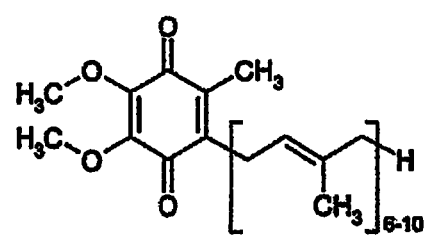

COMPOSITION FOR TREATMENT OF NEURODEGENERATIVE DISEASE

CROSS RELATED APPLICATIONS

This application is a continuation of U.S. patent application Ser. No. 14/652,345 filed Jun. 15, 2015 which is a U.S. 371 National Phase Appln. of PCT/US2014/013002 filed Jan. 24, 2014 which claims priority to U.S. Provisional Appl. No. 61/756,824, filed Jan. 25, 2013, which is hereby incorporated by reference in its entirety.

FIELD OF THE INVENTION

The field relates to compositions administered to protect against the effects of neurodegenerative diseases and methods of administering the compositions.

BACKGROUND

Patients with neurodegenerative diseases, such as ALS, MS, Parkinson's and Alzheimer's, accumulate glutamate in excessive amounts. Glutamate is an amino acid that serves as a neurotransmitter. One theory is that glutamate exits a dead cell and engulfs adjacent cells causing adjacent cells to die. Glutamate from these dead cells engulfs additional cells causing a cascade effect that is capable of spreading the disease. Glutamate kills nerve cells which affect the control of muscles and paralysis sets in, according to this theory. Another theory is the enzymes that normally break up glutamate are not functioning properly in patients with ALS. This leads to excessive glutamate and a shortage of the metabolites of glutamate. Yet another theory is that transporters do not function to transport glutamate out of the connection between muscle and nerves, leading to a localized excess of glutamate. Excess glutamate causes cell death. No known composition of matter or method is known to prolong the life of ALS patients significantly or to reverse the otherwise irreversible degeneration caused by neurodegenerative diseases. Amyotrophic lateral sclerosis (ALS) is a debilitating motor neuron disease. ALS is characterized by rapidly progressive weakness, muscle atrophy, fasciculation and spasticity, dysarthria, dysphagia, and dyspnea. ALS is one of at least five recognized motor neuron diseases but is the most common of these. Progressive muscular atrophy, primary lateral sclerosis, and progressive bulbar palsy are some of the other motor neuron diseases recognized by researchers. Spinal muscular atrophy is considered by some to be a motor neuron disease. It is known that motor neuron disease is associated with degeneration of upper and/or lower motor neurons. Death of upper and lower motor neurons in the motor cortex of the brain, brain stem and spinal cord is associated with prior development of proteinaceous inclusions within cell bodies and axons. Inclusion scan contain ubiquitin and/or one or more of the following proteins: SOD1, TAR DNA binding protein (TDP-43, or TARDBP), or FUS.

The etiology of ALS has failed to discover a single cause or any cause that provides a direction for successful cures or even treatments that prolong survival more than a modest period. All ALS patients are told to expect their symptoms to become progressively worse, leading to death, usually within a few years, at most.

Literature points to a failure of defenses against oxidative stress, particularly the accumulation of superoxides. However, the cause of oxidative stress build-up is unknown. Possibly, oxidative stress initiates or leads to apoptosis of motor neurons. It remains unclear how the build-up of ubiquitin or other proteins or gene mutations of genes making these proteins causes the onset of ALS, if in fact such mutations are the cause. Evidence does not support an early hypothesis that mutant SOD1 results in lost or compromised dismutase activity. Instead, surprisingly, researchers have put forward an hypothesis that mutant SOD1 results in a gain in function rather than a loss in function. Mice lacking the SOD1 gene do not develop ALS, while mutant SOD1 mice develop ALS. Misfolded protein accumulations of mutant SOD1 have not been found in healthy tissues but have been found only in diseased tissues and at greater concentrations during motor neuron degeneration. See Furukawa Y, Fu R, Deng H, Siddique T, O'Halloran T Disulfide cross-linked protein represents a significant fraction of ALS-associated Cu, Zn-superoxide dismutase aggregates in spinal cords of model mice, Proc Natl Acad Sci USA 103 (18), pp. 7148-53 (2006) ("In the spinal cord of symptomatic ALS-model mice, significant amounts of disulfide cross-linked SOD1 multimers are readily detected in the insoluble fractions; no such high molecular mass (MM) species containing SOD1 are seen in the nonsymptomatic and control mice") ["Furukawa"]. In Furukawa, the hypothesis is that a certain degree of aggregation and subcellular localization of these disulfide-crosslinked aggregate multimers may irreversibly disrupt critical cellular process and initiate cell death signal cascades.

SOD1 mutations cause about 2% of ALS cases overall, and it is presumed that this mechanism is only responsible, if it is responsible, for those 2% of patients with SOD1 mutations. Other studies have found elevated levels of glutamate related to neuron degeneration in neurodegenerative disorders including ALS. However, a drug that targets glutamate transporters, Riluzole, has a limited effect on survival. This indicates that glutamate accumulation may not be the cause or may not be the sole cause of ALS.

Other neurodegenerative diseases, such as Alzheimer's and Parkinson's, are associated with the degeneration of neurons. Generally, all of the neurodegenerative diseases share a degeneration of neurons, without a satisfactory explanation in the literature of the actual cause of the degeneration of neurons. If the cause were known, then successful treatments for these awful diseases would have been forthcoming. Instead, researchers have been unable to find successful cures or even treatments that arrest or reverse the progressive degeneration of motor neurons in ALS patients, the efforts of scientists, researchers and drug companies notwithstanding.

According to WEBMD: a-Ketoglutaric acid (AKG) is used for kidney disease; intestinal and stomach disorders, including bacterial infections; liver problems; cataracts; and recurring yeast infections. It is also used for improving the way kidney patients receiving hemodialysis treatments process protein. Healthcare providers sometimes give AKG intravenously (by IV) for preventing injury to the heart caused by blood flow problems during heart surgery and for preventing muscle breakdown after surgery or trauma. Some athletes take AKG to improve peak athletic performance. Suppliers of AKG as an athletic nutritional supplement claim that AKG—alpha-ketoglutaric acid—might reduce problems associated with too much ammonia (ammonia toxicity) during vigorous physical activity. However, according to WEBMD, so far, the only studies that show a reduction in ammonia toxicity have been performed in hemodialysis patients.

According to a recent study, Willoughby, D S; Boucher T, Reid J, Skelton G, Clark M, Effects of 7 days of argininealpha-ketoglutarate supplementation on blood flow, plasma L-arginine, nitric oxide metabolites, and asymmetric dimethyl arginine after resistance exercise. International Journal of Snort Nutrition and Exercise Metabolism, 21 (4), pp. 291-9 (August 2011), any observed changes in heart rate, blood pressure, blood flow and NOx/NO2 levels were attributed to resistance exercise used in the experimental design and not to AAKG supplementation, although arginine levels were elevated. Another study concluded that "AAKG supplementation may hinder muscular endurance," and "the use of these supplements before resistance training should be questioned." See Greer, B K; B T Jones, Acute arginine supplementation fails to improve muscle endurance or affect blood pressure responses to resistance training. Journal of Strength and Conditioning Research 25 (7), pp. 1789-94 (July 2011).

When referring to dosage, the following terms have the meaning accepted by those of ordinary skill in the art: gms or g means grams; Mg or mg means milligrams for dosing (Mg is an abbreviation used for magnesium when not used for dosing/dosage); SID, sid, q.d, Q.d, qd or QD means once daily; BID or bid or b.d means twice daily; TID or tid or t.d means three times a day; QID or qid means four times a day; PO or po means per os, by mouth, orally; PRN or pm meanspro re nata, as needed; and Vitamin B complex means a combination of thiamine (B1), riboflavin (B2), niacin or niacinamide (B3), pantothenic acid (B5), pyridoxine or pyridoxal or pyridoxamine or pyridoxine hydrochloride (B6), biotin (B7), folic acid (B9) and cyanocobalamin or other cobalamins (B12).

SUMMARY

Compositions for treatment of neurodegenerative disease have been found that arrest and, at least in some instances, reverse the progression of neurodegenerative diseases, such as motor neuron disease, Alzheimer's and Parkinson's in humans. Initial results in mutant SOD1 mice show similar benefits compared to controls, when administered one example of the composition. In one example, an alpha-ketoglutaric acid (AKG), a ketone derivative of glutaric acid, was administered orally to patients suffering from neurodegenerative diseases, such as ALS and Alzheimer's, with the result that patients exhibited fewer symptoms of the diseases. In some instances, progression of the diseases were delayed or even reversed in human patients. In contrast, other treatments did not provide a similar benefit to the patients.

In one example, a composition for use by patients suffering from neurodegenerative disease is administered in an operatively effective dosage based on observations of certain symptoms of a patient. A minimum daily dosage may be specified for an adult, and a schedule may be suggested for increasing the amount of the composition administered during an introductory period in order to monitor the symptoms and to watch for adverse side effects. For example an alpha-ketoglutarate (AKG) is combined with γ-aminobutyric acid (GABA) in therapeutically effective amounts to reduce or reverse symptoms of neurodegenerative diseases, such as motor neuron disease.

Alternatively, a baseline dosage of a plurality of substances is packaged for use on a daily or more frequent basis to provide the most essential substances needed to treat a neurodegenerative disease such as ALS. Additional amounts of any or all of three substances and/or other substances may be provided, separately or within the same package, such as a tablet, caplet, capsule, liquid, lozenge, sublingual film, food, drink or the like. Packaging a serving in a single serving package for easy consumption is an improvement over requiring the patient to prepare a serving and surprisingly increases effectiveness of a therapy by increasing convenience of compliance. The additional amounts may be administered based on body mass, activity and/or observation of a patients symptoms, over and above the baseline product taken on a daily or more frequent basis.

The anion of alpha-ketoglutaric acid is alpha-ketoglutarate, which is a de-amination of glutamate, and is an intermediate in the Krebs cycle. alpha-ketoglutarate is transaminated in vivo, along with glutamine, to form an excitatory neurotransmitter, glutamate. According to the literature, an accumulation of glutamate is thought, according to one hypothesis, to be responsible for degeneration of motor neurons in ALS. Normally, the human body decarboxylates glutamate, when vitamin B6 is present, into the inhibitory neurotransmitter gamma aminobutyric acid (GABA).

Arginine-alpha-ketoglutarate (AAKG) is a salt of arginine and alpha-Ketoglutaric acid. This is the form of alpha-ketoglutaric acid that is used by some athletes as a nutritional supplement, without any scientific evidence of any efficacy.

For example, AAKG may be administered with one or more of gamma aminobutyric acid (GABA), glutathione, ubiquinol, coenzyme Q10 (i.e. a form of), methyl folic acid, glysine, magnesium, OptiZinc® zinc monomethionine[1] complex (ratio of 1:1), phosphatydalcholine, taurine, theanine, vitamin D, vitamin D3, magnesium-a-Ketoglutaric acid (MAKG), potassium-a-ketoglutaric acid (PAKG), NADH, B complex, B propolis, 5-hydroxy tryptophan, Cysteplus® N-acetylcysteine[2], *Ginko biloba*, creatine or combinations of these. Many combinations and variations of these have been tested with varying degrees of success.

[1] OptiZinc is a trademark of InterHealth Nutraceuticals Incorporated.
[2] Cysteplus® is a trademark of Thorne Research, Inc.

Surprisingly, compositions comprising one of AAKG, PAKG, MAKG or a combination thereof in combination with one or more of the other ingredients have resulted in reversal of symptoms and/or delay in the progression of neurodegenerative diseases, such as ALS and Alzheimer's.

It is thought, without being limiting in any way, that the compositions provide neurons with energy preventing apoptosis of neurons, such as motor neurons in the case of ALS, that would otherwise occur due to a lack of available, usable energy by these neurons. The same mechanism appears to be therapeutically beneficial for a variety of neurodegenerative diseases, such as ALS, Alzheimer's and Parkinson's.

Use of the compositions for treating neurodegenerative diseases is indicated as a therapeutic treatment but not a cure. It has been observed that withdrawal of AKG for a short period (a few days) results in return of symptoms of ALS. Therefore, it is believed, without being limiting in any way, that AKG does not reverse damage caused to motor neurons. Instead, supports the hypothesis that the compositions stabilize motor neuron health by providing energy to the motor neurons, preventing continued abnormal apoptosis caused by a motor neuron disease. Results do not appear to be limited to one type of motor neuron disease and generally have improved the health of human patients suffering from various neurodegenerative diseases. The most successful combinations each included a type of AKG, e.g. a compound comprising AKG as a salt or other orally administered composition.

In addition to the administration of compounds containing AKG, the following have shown synergistic effects: daily massage of atrophic muscles with coconut oil, e.g. virgin coconut oil; biweekly total body massage with coconut oil; coconut oil and MCT administered per os; and combinations of these.

Coconut oil is mixed to tolerance with MCT for oral consumption. This coconut oil, MCT mixture may not be tolerated well by some patients. For example, side effects may include mild diarrhea or stomach upset. It is recommended that the mixture be introduced at low dosages (e.g. teaspoon daily) and increased only if well tolerated.

In addition, resistive exercise, physiotherapy, aerobic exercise, stretching and range of motion exercises may be therapeutically beneficial, provided that patients do not exercise to fatigue.

In one example, a composition containing AKG and a compound supporting stem cell health and/or generation may provide a synergistic effect. It is thought, without be limiting in anyway, that the composition containing AKG prevents or slows abnormal apoptosis (i.e. programmed cell death), while the compounding supporting stem cell health replaces neurons lost through the neurodegenerative process of the disease. For example, a combination of one or more of carnosine, green tea extract, blueberry extract and Vitamin D3 synergistically stimulates stem cells while a composition containing AKG prevents or slows abnormal degeneration of existing neurons. In specific human ALS patients, this combination has resulted in surprising and unexpected improvement in both strength and endurance and apparent reversal of the motor neuron degeneration, synergistically, by the combination of a composition comprising AKG and other metabolic support constituents with a composition containing constituents supporting stem cell health and stem cell generation.

In another example, stem cell replacement therapy maybe combined with administration of a compound comprising AKG in neurodegenerative diseases, such as Alzheimer's and ALS. For example, stem cells injected into cerebrospinal at the base of the spine of rats, injured by a neuron destroying virus to simulate the damage caused by ALS, have shown the ability to recover partial use of limbs. See Vastag B, Stem cells step closer to the clinic: paralysis partially reversed in rats with ALS-like disease, JAMA 285 (13), pp. 1691-3 (April 2001). More recently, Mazzini, L.; Fagioli, F; Boccaletti, R; Mareschi, K; Oliveri, G; Olivieri, C; Pastore, I; Marasso, R; Madon, E; Stem cell therapy in amyotrophic lateral sclerosis: a methodological approach in humans, Informa Healthcare, Vol. 4, No. 3, pp. 158-161 (2003) reported intraspinal cord implantation of autologous mesenchymal stem cells (MSCs) in a few human patients. Bone marrow collection was performed according to the standard procedure by aspiration from the posterior iliac crest. Ex vivo expansion of mesenchymal stem cells was induced according to Pittenger's protocol. The cells were suspended in 2 ml of autologous cerebrospinal fluid and transplanted into the spinal cord by a micrometric pump injector. The outcome was positive, a slowing of progression of the symptoms of ALS, but no reversal of symptoms was reported.

BRIEF DESCRIPTION OF THE DRAWINGS

The following drawings are illustrative examples and do not further limit any claims that may eventually issue.

FIG. 1 is a chemical formula for α-ketoglutaric acid, from which the anion α-ketoglutarate is capable of being combined with arginine, glycine, magnesium and other substances to form a salt, such as arginine α-ketoglutarate (A-AKG or AAKG), for example.

FIG. 2 is a chemical formula for Idebenone, a synthetic form of coenzyme Q10 that may be substituted for coenzyme Q10.

FIG. 3 is a chemical formula for ubiquinol another form of coenzyme Q10 that may be substituted for coenzyme Q10.

FIG. 5 is a chemical formula for γ-Aminobutyric acid (GABA).

FIG. 6 is a chemical formula of coenzyme Q10.

When the same reference characters are used, these labels refer to similar parts in the examples illustrated in the drawings.

DETAILED DESCRIPTION

Figure 4:
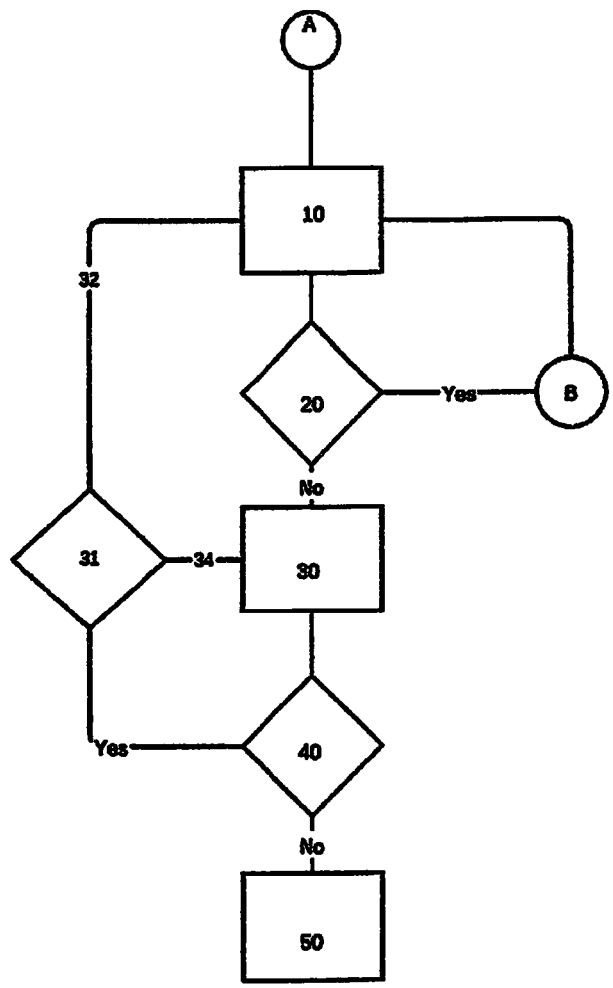
FIG. 4 is a flow diagram illustrating an example of a method for treating neurodegenerative diseases.

Warning: the Deanna Protocol or any other example provided should not be used without consultation with a physician, should not be used by women who are pregnant or may become pregnant, by any person using other medications without consultation with a physician, especially medications for hypertension or stimulants, and should not be taken with alcohol.

This detailed description provides examples that are not intended to be limiting to the claims that eventually issue, and the invention includes combinations and variations of examples provided. For example a composition of matter comprises an AKG, such as illustrated by the formula in FIG. 1. FIGS. 2 and 3 illustrate additional examples of molecules, which may be added to the composition, providing a synergistic effect. For example, Idebenone may be added to the composition. Alternatively, instead of idebenone or in addition, a coenzyme Q10 may be added to the composition. For example, the Ubiquinol form may be added to the composition. It is believed, without being limiting many way, that the Ubiquinol form scavenges superoxides more efficiently than other forms, for example.

In one example, the following protocol (Deanna Protocol—a trademark of Winning the Fight, inc.) is prescribed and administered for patients suffering from a neurodegenerative disease, such as ALS, motor neuron diseases, multiple sclerosis, Alzheimer's and Parkinson's: AAKG not to exceed 18 gms q.d, gamma aminobutyric acid (GABA) 250 mgbid, Glutathione 175 mg 2 tid, ubiquinol 200 mg bid, creatine 850 mg bid, Glutathione 3000 mg intravenous once a week, Co-Q10 as directed (up to 100 Mg q.d). Methyl folic acid [5-MTHF] 1 mg bid, glysine 500 mg bid, magnesium 400 mg q.d, OptiZinc® zinc monomethionine[3] complex (ratio of 1:1) 30 mg q.d, phosphatydalcholine 420 mg 2 bid, taurine (i.e. 2-Aminoethylsulfonic Acid) 200 mg bid, theanine (i.e. 5-N-ethylglutamine) 200 mg q.d, vitamin D 10,000 1U q.d, vitamin D3 5,000 1U q.d. magnesium-potassium-AKG 1.9 gms PO prn (e.g. 20 gms q.d), nicotinamide adenine dinucleotide hydrate (NADH) 20 mg bid, B complex as directed, B propolis 500 Mg q.d, 5-hydroxy tryptophan 50 mg q.d. PM, Cysteplus® N-acetylcysteine"[4] 500 mg q.d, *Ginkgo biloba* 120 mg q.d. Daily massage of atrophic muscles with virgin coconut oil. Biweekly total body massage with virgin coconut oil Coconut oil mix to tolerance with medium chain triglycerides oil (MCT) for oral consumption dose to tolerance. Exercise: resistance, aerobic, stretching and range of motion exercises for affected joints. Care should be taken to not exercise to fatigue.

[3]OptiZinc is a trademark of InterHealth Nutraceuticals Incorporated.
[4]Cysteplus® is a trademark of Thorne Research, Inc.

Surprising and unexpected results included marked reduction in fasciculation and spasticity, dysarthria, dysphagia, and dyspnea of ALS patients and improved mobility and cognitive function in a patient with Alzheimer's. In one example, additional benefit was provided by sustained release of AKG. A human patient taking AKG supplement hourly during waking hours showed a marked improvement compared to ingesting AKG only four times per day.

In another example, the Deanna Protocol (trademark of Winning the Fight, inc.) or another composition for treatment of a neurodegenerative disease is combined with Neupogen [G-CSF] or Leukine [GM-CSF] for stimulating stem cell generation. In yet another example, a combination of one or more of carnosine, green tea extract, blueberry extract and Vitamin D3 synergistically stimulates stem cells while a composition containing AKG prevents or slows abnormal degeneration of existing neurons. For example, carnosine, green tea extract, blueberry extract and vitamin D3 were combined with AAKG, MAKG, PAKG or combination thereof in a supplement for administration per os (Combined Supplement). For example, a complex of MAKG and PAKG may be compounded and may be administered in a dose greater than 20 mg q.d per os. The Combined Supplement (which may be a core composition, a baseline composition or the like) may be administered in doses up to the maximum tolerable dosage of the patient once, twice, three times or four times per day, as necessary. The supplement may be combined with coconut oil massage and resistive exercise to reduce symptoms of ALS.

In another example, stem cell therapy may be combined with the Deanna Protocol (trademark of Winning the Fight, inc.) or another protocol utilizing a compound comprising AKG. For example, bone marrow collection may be performed according to the standard procedure by aspiration from the posterior iliac crest. Then, ex vivo expansion of mesenchymal stem cells may be induced according to Pittenger's protocol. These cells may be suspended in 2 ml of autologous cerebrospinal fluid and transplanted into the spinal cord by a micrometric pump injector. In one example, the Combined Supplement is administered in combination with the stem cell therapy. For example, coconut oil massage may be performed topically one time each week or more often for muscular dystrophy and ALS patients, and administration of coconut oil and/or MCT oil may be administered per os up to the amount tolerated by the patient for ALS, Alzheimer's and other neurodegenerative diseases.

In one example, 250 mg of GABA was administered three times per day per os, 30 mg of NADH was administered twice per day sublingually, and 3 grams of AAKG were administered, initially, four times per day per os, with the dosage gradually increasing up to 18 grams, if tolerated by the patient. Alternatively, one or a combination of MAKG or PAKG could be substituted or added to the dosage of AAKG, as tolerated, if blood levels of arginine exceed tolerated levels.

In one example a composition for the treatment of neurodegenerative diseases comprises 2-amino-5-(carbamoylamino)pentanoic acid—AKG (L-CAKG), known as L-Citrulline Alpha Ketoglutarate by body builders. L-CAKG may be substituted for AAKG. In yet another example, creatine ethyl ester—AKG (CEE-AKG) may be used as a substitute or to supplement AAKG in a composition for treatment of neurodegenerative diseases. CEE-AKG is a mixture of esterified creatine and creatine AKG. For example, a dose of CEE-AKG may comprise 1 gram of creatine ethyl ester HCL and 200 mg of creatine-AKG in the form of a pill or capsule for administration per os.

In one example, a combination of AAKG and sublingual NADH provides a synergistic effect. In one example, a non-sublingual administration of NADH was ineffective, compared with sublingual administration of NADH. Specifically, a combination of AAKG and NADH provides a more significant reduction in fasciculation and spasticity than either composition administered alone, regardless of dosage selected. For example, a chemical composition administered as provided in Example A of Table A provides a surprising and unexpected reduction in fasciculation and spasticity. The composition of Example B provides additional benefits that reverse the symptoms of ALS including dysarthria, dysphagia, and dyspnea. The same or similar protocol administered to a human Alzheimer's patient allowed a patient incapable of movement to sit up in bed and to communicate. Example C shows a protocol substituting other types of AKG for AAKG, such as a mixture of magnesium and potassium salts instead of an L-arginine, based AAKG. The omission of sublingual NADH in Example C reduces effectiveness compared to a combination of a source of AKG and NADH.

A dosage of AKG of only six to eight grams resulted in some improvement in a patient with a neurodegenerative disease, but an increase in dosage and sustained release is an improvement compared to this sub-optimal dosage. In Example A of Table A a sustained release formulation of arginine alpha-ketoglutarate is preferred. In example B, the AAKG was administered hourly during waking hours, which resulted in marked reduction in symptoms of ALS.

In one example, taking 6 grams of AAKG once per day resulted in reduced sweating during exercise but had no effect on fasciculations or parathesias in humans. In another example, taking 18 grams of AAKG in four doses over the course of a day, and a pill containing AKG once per hour, at least 100 milligrams per pill, resulted in reduced fasciculations and reduced parathesias in humans, especially when combined with sublingual administration of NADH, gamma-aminobutyric acid, and at least one form if a CoQ10, such as ubiquinol, coenzyme Q10, Neurochondria, or idebenone, preferably each in one of the dosages suggested in Table A (at the end of the specification), for example. A synergistic effect surprisingly resulted in increased strength, reduced fatigue and an improvement in other symptoms of ALS. In one example, enterically coated NADH is administered per os instead of sublingually and maybe compounded and administered together with a source of AKG for release within the intestines, such as the small intestine and/or the large intestine.

For example, food/supplements/medical foods may be combined with enzymes, non-exhausting exercise, massage and an antioxidant, for example, in a protocol intended to support and improve the health of patients with a neurodegenerative disease, such as ALS, Alzheimers, Parkinsons or muscular distrophy.

In one example, an alpha ketoglutarate (AKG), such as a salt or other palatable form of AKG, may be included as one substance in a composition for use by patients diagnosed with a neurodegenerative disease. It is believed, without being limiting in any way, that all patients suffering from neurodegenerative diseases suffer from a metabolic disorder that affects the Krebs cycle. By administering AKG, a metabolite necessary for the metabolic process, patients that suffer from an inability to metabolize glutamate efficiently nevertheless have sufficient AKG at the cellular level to prevent or retard abnormal cell death or premature apoptosis, presumably. Studies in ALS mice have shown a very significant prolongation of life using a composition including AKG compared to other protocols omitting AKG as a dietary supplement.

For example, an arginine alpha ketoglutarate (A-AKG or arginine-AKG) is included in a composition to be used by patients with a neurodegenerative disease at a baseline dosage. Human patients taking AKG showed marked, obvious improvements in their neurodegenerative symptoms relating to ALS, Alzheimers and Muscular Distrophy. When AKG was withheld from a patient, symptoms returned, only to show improvement again, when AKG was recommenced.

In one example, a gamma-amino butyric acid (GABA) may be added to the composition containing the AKG. GABA is an inhibitory neurotransmitter in the human central nervous system and regulates nerve cell excitability throughout the nervous system. GABA may be purchased from Now Foods.

In one example, Coconut oil and/or a caprylic acid is added as another substance in the composition. In one example, coconut oil may be massaged once a day into all the muscles of the body of an ALS patient. For example, 100% pure and extra virgin coconut oil may be purchased from Nutiva. Coconut oil liquifies at 76 degrees, for example. It is believed that caprylic acid, a constituent of the coconut oil, is absorbed through the skin and into the muscles and/or perhaps the circulatory system. Alternatively, or in addition to coconut oil massage, a caprylic acid is added to a composition for oral administration to patients suffering from neurodegenerative disorders.

It is thought, without being limiting in any way, that AKG is a metabolite of glutamate, when glutamate is acted upon by enzymes. If the enzymes necessary to metabolize glutamate are absent or present in amounts too low to effectively metabolize glutamate, then a sufficient quantity of AKG would be unavailable for producing energy that can be used by the cells, such a neurons, and these cells starve for lack of energy and die. For example, it is thought that certain genes that produce enzymes that are necessary for this process are dysfunctional, resulting in an excess of glutamate and shortage of AKG.

In A-AKG, arginine is added to AKG to make it palatable. Other forms of AKG may be used that are palatable, provided that the AKG is capable of being delivered to the cells that need AKG in the body.

In one example, too little GABA results in nerve cell excitability or unregulated excitability throughout the nervous system. Administering GABA as a supplement is observed to restore muscle tone and control nerve cell excitability, which exhibits as diminished muscle spasticity in patients with neurodegenerative diseases, such as ALS.

Enzymes that are used in the metabolism of AKG are CoQ10, which may be provided by the supplements Ubiquinol and NADH or their precursors Niacin and 5-hydroxy tryptophan [5-HTP].

A method of treating a patient with neurodegenerative disease may include the following:

Exercise: daily, non-exhausting, exercise which should include range of motion exercises, aerobic exercise, stretching, breathing exercises and hand exercises. One thing exercise does is cause the secretion of neurotransmitters at the muscle nerve junction.

Antioxidant: administration of glutathione. Glutathione is an antioxidant that is good for the nervous system. The best method of delivery is Intravenous and this should be done at least once a week. There is also a fat soluble form and a suppository form if intravenous application is not available.

A-AKG comes in the form of both tablets and powder. The powder can be dissolved in any number of liquids including water, orange juice or chocolate milk. A recommended baseline dosage is 18 grams a day; administered as 6 grams three times a day. Preferably, gradually increase from 2 to 6 grains three times a day as the lower dose is shown to become tolerable. If diarrhea occurs at any time lower the dose until symptoms subside then increase the dose until the patient's muscle symptoms are suppressed, such as fasciculation's, twitching, tremors, and cramps. Adding another source of AKG capsules orally every hour while awake until muscle symptoms subside is beneficial, as the amount of arginine administered by taking arginine 1:1 with AKG above 18 grams per day is not recommended. The degree of muscle symptoms present determine the dose of AKG to be taken.

For example, GABA is available in capsules, chewable tablets and liquid-form. A recommended administration is 250 mg twice a day. Enough GABA should be taken to stop spasticity. Ubiquinol comes in soft-gels and administration may be 400 mg three times a day. Niacin [non flush] comes in capsules and administration may be 250 mg twice a day. A 5-hydroxy-tryptophan supplement is available in capsules and administration may be 50 mg twice a day.

Glutathione comes in intravenous, capsule and suppository form and administration by intravenous delivery may be 2,000 mg to 3,000 mg once a week, or in pill form 525 mg twice a day, in a delayed release (Thorne) form that passes the stomach and is absorbed in the intestine, preferably lower intestine.

Three nutritional supplements may be combined in a liquid, powder or tablet composition taken three times per day, according to the following composition per oral administration: 3-9 grams of an AKG, such as 6 grams of A-AKG, if muscle symptoms appear or continue, take additional AKG, such as in a capsule form, as frequently as possible, such as every hour while awake, until muscle symptoms resolve; a range of 50 to 140 mg of GABA, additional GABA may be administered above the baseline dosage until spasticity subsides; 100 to 400 mg of Ubiquinol and/or Co-Q-10; 100 to 200 mg of Niacin; 20 mg of 5-hydrotryptophan; 200-400 mg of an antioxidant, such as Glutathione, in a form capable of being absorbed into the blood stream, alternatively or in addition, an intravenously administered Glutathione may be administered weekly. For example, 73% of ALS patients under the care of a physician were able to stop the degeneration or improve their condition, using this protocol, a very surprising and unexpected result, given that two hundred years of research has been unable to achieve any comparable results. A clinical study of ALS mice was conducted for the applicant at the University of South Florida and concluded the protocol "produces a beneficial effect in ALS mice and is a feasible strategy that may prolong survival and quality of life of ALS patients."

Neurodegenerative diseases are aggressive and fatal, and there is was no other treatment that has shown an ability to delay the progression of neurodegeneration for more than a few months (in human time). The composition and method for treating neurodegenerative disease has proven to be an effective therapy in mice and humans for ALS, and in humans with Alzheimers and other neurodegenerative diseases.

In one example, a core product, recommended to be administered three times daily, contains the following ranges of active ingredients, not including excipients, stabilizers and taste enhancers, for a serving of a powdered or liquid composition suitable for oral delivery: 2 to 6 grams of an AKG, such as A-AKG; 200 to 1,200 mg of Ubiquinol; 100 to 200 mg of GABA and 50 to 100 mg of Niacin. For example, 6 grams of AKG is included in each serving, administered three times daily, preferably some or all of the AKG being in the form of a magnesium-AKG salt and/or a glycine-AKG, in order to improve palatability of the composition compared to A-AKG. If A-AKG alone is used as a source of AKG, then an amount of AKG provided per serving may be limited to 2 grams per serving, and additional AKG may be administered by capsule, tablet, liquid or powder hourly as needed to control muscle symptoms. In one example, a core composition comprises from 2 to 6 grams of AKG per serving and at least 100 mg of GABA. Preferably, a form of coenzyme Q10 is added to the core composition for neurodegenerative diseases such as ALS and Parkinsons to control symptoms associated with these diseases. For example, 100 mg per service on a form of coenzyme Q10 may be added to the core composition.

In an example of a method of administering a composition for treating a neurodegenerative disease, FIG. 4 illustrates a flow diagram for illustrating the method. The method starts at A, when a patient is diagnosed or suspects a neurodegenerative disease is causing muscle or nervous symptoms. An initial baseline composition 10 is prescribed for the patient that contains an α-ketoglutarate (AKG), a form of coenzyme Q10 (CoQ10), and a source of γ-Aminobutyric acid (GABA). For example, the initial baseline composition would include from 1 to 3 grams of an AKG, such as arginine-AKG, 100 to 1,000 mg of a form of a CoQ10, such as ubiquinol; and 100 to 200 mg of GABA. For example, one example uses a composition of 2 grams of arginine-AKG, 200 mg of ubiquinol and 200 mg of GABA. This dosage may be taken three times daily for a period of time, such as a week, while observing 20 any change in symptoms and any adverse side effects. If adverse side effects occur in a patient, then the physician must determine whether to discontinue administration, change the composition or continue at the dosage for an additional period. If the side effects are manageable or no adverse side effects occur, then a higher dosage of AKG may be administered 30 for a period of time, such as a week. The higher dosage of AKG may be added to the composition or may be taken in a separate composition. Preferably, at least a portion of the additional dosage is taken hourly during waking hours. Again, the patient observes symptoms and side effects. If side effects are observed at the higher dosage 40, then the severity of adverse side effects must be considered 31. If severe, then the dosage to the patient returns to the lower dosage 10. If not severe and the benefit in reduction of symptoms outweighs the adverse side effects, then the patient may remain at the higher dosage 40. If no adverse side effects occur and the symptoms of the patients have not abated, then an even higher dosage may be administered 50 based on the patients observations of the patient's own symptoms in order to control the symptoms of the neurodegenerative disease. The patient can control the correct dosage 50 that is needed to control his or her symptoms, which may vary with the amount of exercise and other external factors affecting the level of AKG needed by the patient's body.

Results for people with various neurodegenerative diseases have shown that a core composition taken three times daily can provide a combination of supplements that are needed by the patients. The combination of substances in the core composition synergistically provide nutrition at the metabolic, cellular level substantially reducing symptoms and increasing longevity compared to other therapies that do not provide the substances provided in the core composition.

Variations and combinations of constituents illustrated in the examples are included within the scope of the inventions. For example, compounds maybe substituted and combined in a protocol known as the Deanna Protocol (trademark of Winning the Fight, inc.) for use in patients suffering from neurodegenerative diseases, such as motor neuron diseases and Alzheimer's, for example.

Obvious combinations and variations of the examples, based on the teachings of this disclosure, are intended to be within the scope of the claims that eventually issue. This detailed description provides examples including features and elements of the claims for the purpose of enabling a person having ordinary skill in the art to make and use the inventions recited in the claims. However, these examples are not intended to limit the scope of the claims, directly. Instead, the examples provide features and elements of the claims that, having been disclosed in these descriptions, claims and drawings, may be altered and combined in ways that are known in the art.

TABLE A

| CONSTITUENT | DOSAGE | | |
|---|---|---|---|
| | Example A | Example B | Example C |
| arginine alpha keto-glutarate | 10 g | inc. gradually to 18 g | — |
| Mg-alpha keto-glutarate | 10 g | 0 g | 10 g |
| K-alpha keto-glutarate | 10 g | 0 g | 10 g |
| NADH (sublingual) | 20 mg | 20 mg 2 × day | 0 mg |
| gamma-aminobutyric acid[5] | 250 mg | 250 mg 2 × day | as tolerated |
| glutahione | 175 mg 3 × day | 350 mg 3 × day | 0 mg |
| Idebenone | — | | 180 mg |
| ubiquinol | | 200 mg 2 × day | — |
| coenzyme $Q_{10}$ | 200 mg | — | — |
| vitamin B complex | — | — | 400 mg |
| bee propolis | | 500 mg | |
| 5-hydroxy tryptophan | | 50 mg | |
| creatine | | 879 mg 2 × day | |
| cysteplus | | 500 mg | |
| ginko biloba | | 120 mg | |
| glutathione | | 3000 1 × week | |
| glycine | | 500 mg 2 × day | |
| magnesium | | 400 mg | |
| methyl folic acid (5-MTHF) | | 1 mg 2 × day | |
| Neurochondria[6] | | | 1 pill daily |
| Opti Zinc[7] | | 30 mg | |

TABLE A-continued

| | DOSAGE | | |
|---|---|---|---|
| CONSTITUENT | Example A | Example B | Example C |
| phosphatidylcholine | | 840 mg 2 × day | |
| taurine | | 500 mg 2 × day | |
| theanine | | 200 mg | |
| vitamin D3 | | 5000 IU | |
| vitamin D | | 10,000 IU | |

[5]PharmGABA > 250 gamma-aminobutyric acid is a trademark of Thorne Research, Inc.
[6]Neurochondria is a registered trademark of Thorne Research, Inc. and includes within a single pill 1500 micrograms (mcg) of B12; 300 mcg of folate; 250 mg of benfotiamine; 150 mg of Coenzyme Q10; 120 mg of R-lipoic acid; 150 mg of glutathione; 300 mg of acetyl-L-carnitine; 150 mg of phsophatidylserine, which support neuron metabolism.
[7]OptiZine is a registered trademark of InterHealth Nutraceuticals Incorporated.

What is claimed is:

1. A method of treating a motor neuron disease in the brain, brain stem, and spinal column comprising: administering 3 times a day a base composition with 3-9 grams of alpha-ketoglutarate and an amount of gamma-aminobutyric acid (GABA) of at least 50 mg and not more than 140 mg per serving of the composition, wherein the GABA has the chemical formula:

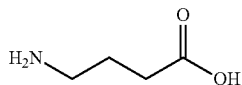

with a free amino group and a free carboxylic acid group when dissolved in water.

2. The method of claim 1, wherein the base composition further comprises a therapeutically effective amount of a form of coenzyme Q10.

3. The method of claim 2 wherein the base composition further comprises a nicotinamide.

4. The method of claim 3, wherein the nicotinamide comprises NADH.

5. The method of claim 3, wherein the nicotinamide comprises niacin.

6. The method of claim 1, wherein the alpha-ketoglutarate comprises an arginine-alpha-ketoglutarate.

7. The method of claim 1, wherein the alpha-ketoglutarate comprises a glycine-alpha-ketoglutarate.

8. The method of claim 1, wherein the alpha-ketoglutarate comprises a magnesium-alpha-ketoglutarate.

9. The method of claim 3, wherein the base composition further comprises a caprylic acid.

10. The method of claim 1, further comprising packaging each serving of the base composition in single serving packages.

11. The method of claim 1, further comprising preparing the base composition by combining a source of the alpha-ketoglutarate (AKG) in a therapeutically effective amount with a source of the gamma-aminobutyric acid (GABA) in a therapeutically effective amount as constituents in a powder mixture or liquid serving mixture.

12. The method of claim 1, further comprising administering a stem cell therapy for increasing the number motor neurons in a patient.

13. The method of claim 12, further comprising administering a therapeutically effective amount of a form of coenzyme Q10.

* * * * *